(12) United States Patent
Dinkelis et al.

(10) Patent No.: US 6,908,305 B2
(45) Date of Patent: Jun. 21, 2005

(54) ORTHODONTIC FACEBOW

(75) Inventors: Vladimir Dinkelis, Jerusalem (IL); Yull Lozinski, Jerusalem (IL); Boaz Tsur, Jerusalem (IL)

(73) Assignee: Alina Lozinski, Jerusalem (IL)

( * ) Notice: Subject to any disclaimer, the term of this patent is extended or adjusted under 35 U.S.C. 154(b) by 161 days.

(21) Appl. No.: 10/387,034

(22) Filed: Mar. 11, 2003

(65) Prior Publication Data

US 2003/0175651 A1 Sep. 18, 2003

(30) Foreign Application Priority Data

Mar. 12, 2002 (IL) .............................. 148,627

(51) Int. Cl.⁷ .............................. A61C 3/00
(52) U.S. Cl. .............................. 433/5; 433/22; 433/17
(58) Field of Search .............................. 433/17, 5, 22, 433/18, 19; 24/593.1, 594.1

(56) References Cited

U.S. PATENT DOCUMENTS 3,313,135 A  * 4/1967 Reisner .............................. 70/408
4,087,915 A    5/1978 Andrews .............................. 32/14 D
4,588,380 A    5/1986 Toll .............................. 433/5
4,764,110 A    8/1988 Dougherty .............................. 433/5
5,551,871 A  * 9/1996 Besselink et al. .............................. 433/5
5,695,332 A    12/1997 Samuels .............................. 433/5

* cited by examiner

Primary Examiner—Cary E. O'Connor
Assistant Examiner—Candice C Stokes
(74) Attorney, Agent, or Firm—Schneck & Schneck; Thomas Schneck

(57) ABSTRACT

The invention provides an orthodontic facebow of the type having an inner bow consisting of two inner arms, each including an end portion, and an interconnected outer bow consisting of outer arms, characterized in that the free end portions of each inner arm is split and fitted with a ratchet type enlargement so as to allow it to be easily inserted into a tube connected to a band affixed to a tooth, while preventing disengagement therefrom without the enlargements being squeezed together.

5 Claims, 2 Drawing Sheets

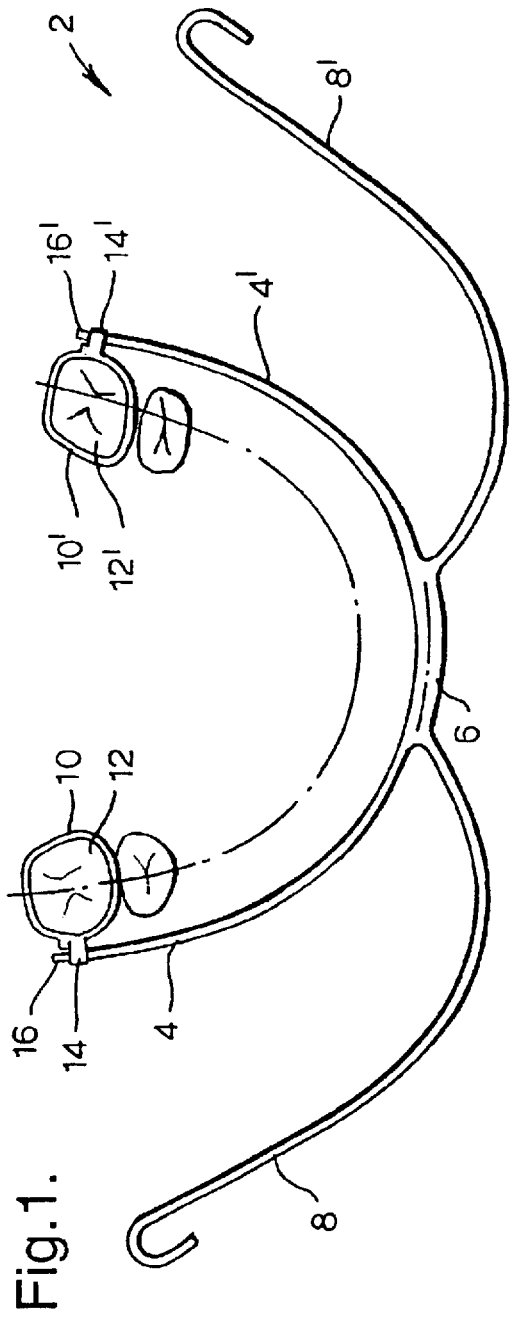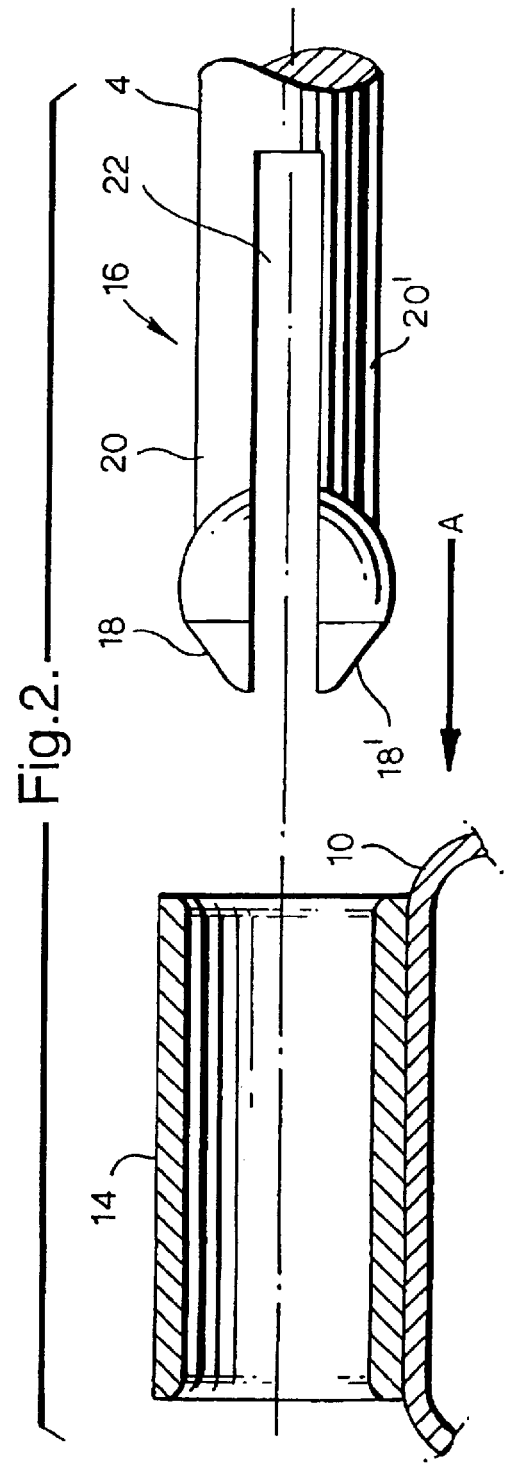

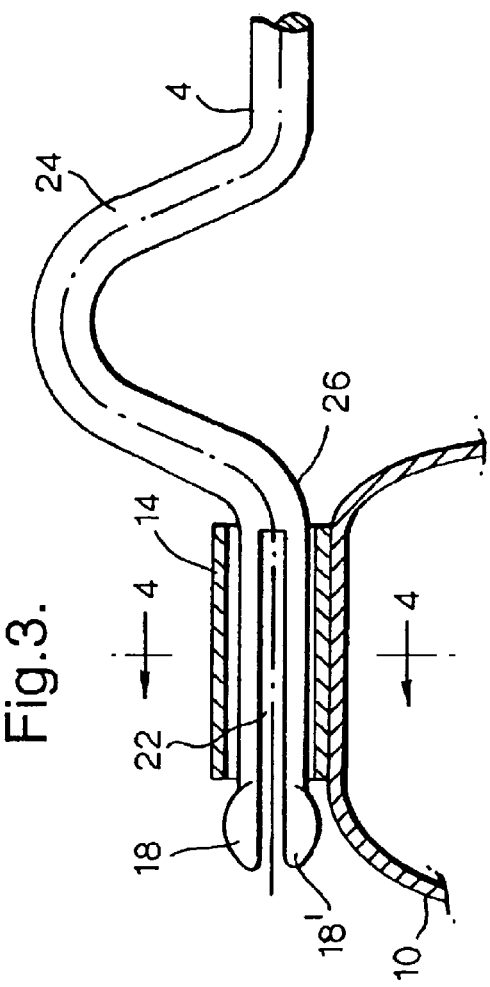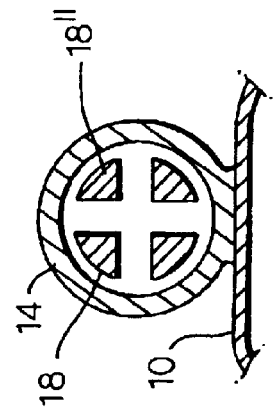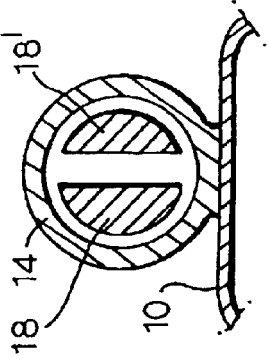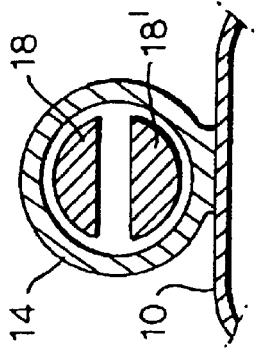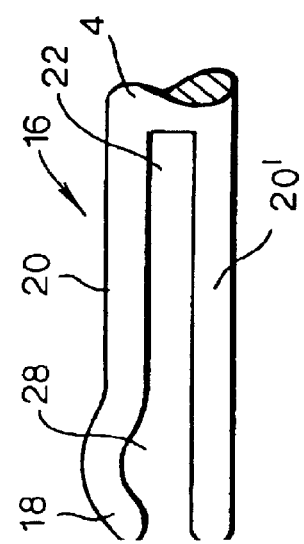

ORTHODONTIC FACEBOW

BACKGROUND OF THE INVENTION

The present invention relates to an orthodontic instrument, particularly to a facebow for use in orthodontic treatment. More specifically, the invention relates to fixing tips for such facebows.

FIELD OF THE INVENTION

As described in column 1 of U.S. Pat. No. 5,695,332 (Samuels), facebows are used in orthodontics to move pairs of molar teeth distally in a patient's mouth. In accordance with usual practice, a metal band is cemented in position around each of the teeth which are to be either moved distally or restrained against forward movement. Each metal band has a buccally projecting bracket fixed to it, as by welding. The metal band includes a tube having a longitudinal opening therethrough, the longitudinal central axis of which is directed forward along the buccal surface of the molar teeth.

The facebow comprises a C-shaped inner metal bow having opposite ends or feet which engage with the tubes of the aforementioned brackets. In use, the inner bow extends around the outer labial and buccal portions of the patient's teeth inside the mouth. The facebow further comprises an outer bow which is joined at its middle to the middle of the inner bow. The outer bow has arms which extend posteriorly around the outside of the patient's cheeks. The free ends of the arms of the outer bow are provided with hooks, to which is attached an elasticized or spring-loaded strap connected around the back of the head and/or neck of the patient. The facebow is thus pulled posteriorly by the strap; because the face bow is fixed to the patient's teeth, a distal force is applied to the teeth. Over a period of time, the teeth are moved distally, or alternatively, are held against forward movement. The facebow is held to the teeth merely by way of the ends of the inner bow within the tubes of the brackets. The tension developed by the head/neck strap keeps the inner bow in engagement with the brackets on both teeth (U.S. Pat. Nos. 4,087,915; 4,588,380; 4,764,110).

Should the strap break or become detached from the facebow for any reason, then the inner bow is free to disengage from the brackets, especially while the patient is asleep. This could be dangerous because the ends of the inner bow are relatively sharp and could possibly penetrate the user's check, or even an eye, during sleep.

Facebows have been proposed which include a locking catch on each arm of the inner bow: an end portion of the locking catch snap-engages behind a projection on the bracket which is affixed to the tooth. Facebows having different locking catches have a generally particular shape, but different sizes and construction of the brackets vary from one manufacturer to another.

U.S. Pat. No. 5,695,332 discloses a facebow comprising an inner bow supplied with holding appliances constructed as U-shaped loops, similar to a haberdashery pin, made of spring wire and mounted by soldering or welding to the respective arms of the inner bow.

The locking catch is effective in preventing accidental removal of the facebow, however, all of the known locking catches have some shortcomings. The locking catches are not easy to use. They are difficult to put in and out of place and may present a real danger in cases of emergency, for instance, if the user of the facebow is unconscious and a third party, who is not familiar with the locking catch system, has to take the facebow out of the user's mouth. Furthermore, if the user of the facebow accidentally crashes into something and the facebow gets stuck, the only way to detach it would be by pulling out the teeth which are attached to the facebow. There are definite difficulties involved in safely releasing such an appliance from a patient's mouth without risking injury to the patient. In addition, the construction of such facebows comprises parts which are soldered or welded to the arms, rendering the appliance complex and expensive.

DISCLOSURE OF THE INVENTION

It is therefore a broad object of the present invention to provide an orthodontic facebow wherein each of the free ends of the inner bow can be easily and quickly connected to, and disconnected from, a band positioned around a tooth.

It is a further object of the present invention to provide an orthodontic facebow having end portions at the free ends of the inner bow which can be easily and quickly inserted into, and removed from, connecting tubes.

In accordance with the invention, there is provided an orthodontic facebow of the type having an inner bow consisting of two inner arms, each having an end portion, and an interconnected outer bow consisting of outer arms, characterized in that the free ends of each inner arm are split into a plurality of arm portions and at least one arm portion is fitted with a ratchet type enlargement so as to allow it to be easily inserted into a tube connected to a band affixed to a tooth, while preventing disengagement therefrom without at least one of said arm portions being squeezed towards the other or others.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a schematic representation of a prior art facebow coupled to a tooth fitted with a band and coupling tube;

FIG. 2 is an enlarged, cross-sectional view of the free end of a facebow arm according to the present invention, in its disengaged state;

FIG. 3 is a view of the free end of the facebow arm of FIG. 2 in its engaged state;

FIGS. 4A, 4B and 4C are cross-sectional views along line 4—4 of FIG. 1, showing three possible embodiments of the free ends of a facebow arm according to the present invention, and FIG. 5 is a side view of a modification of the free ends of the facebow arm shown in FIG. 3.

DETAILED DESCRIPTION

Referring to FIG. 1, there is illustrated a commonly used prior art metallic wire facebow 2, comprising a C-shaped, inner bow consisting of inner arms 4, 4' connected at the middle portion 6 to an outer bow consisting of outer arms 8, 8'. Further seen are metal bands 10, 10' cemented around teeth 12, 12' which bands are provided with coupling tubes 14, 14'. The free ends 16, 16' of the inner arms 4, 4' are inserted into tubes 14, 14' and are affixed in this position by various ways and means, such as those described in the above-mentioned prior art patents.

FIGS. 2 and 3 illustrate a portion of the metal band 10 and attached coupling tube 14, and the free end 16 of an inner arm 4. As seen, according to the present invention, the free end 16 is a ratchet-type, spring-biased end, consisting of two suitably configured edge portions 18, 18', each connected to rod portions 20, 20', separated by a slot 22. The edge portions 18, 18' are carefully rounded so as to assure that injury will not be caused to the user. The maximum diameter of the enlarged portions, when squeezed together, should not exceed the inner diameter of the tube. For connecting the inner arms into the respective tubes, all that is necessary is to push the free end of an inner arm into the respective tube in the direction of arrow A, until the enlarged portions 18, 18' will emerge from the other end of the tube, as shown in FIG. 3. Due to the ratchet-type enlargement of portions 18, 18', an ordinary pulling force against the direction of arrow A will not cause their disengagement. In order to disconnect the facebow, it is necessary to first squeeze together edge portions 18, 18', against the force of the spring action prevailing at the split ends of rod portions 20, 20', and only then to pull back the inner arm.

As further seen in FIG. 3, arms 4 may be bent to form a part of a loop 24 having a knee 26 delimiting the movement of arm 4 inside tube 14 in the direction of arrow A.

FIGS. 4A, 4B and 4C depict three possible embodiments of the quick-connect, easy disengagement coupling between the arms and the tubes, all embodiments possessing the same features as described above with reference to FIGS. 2 and 3 and functioning in a similar manner.

FIGS. 4A and 4B show edge and rod portions split into two enlargements, one along a horizontal plane and the other in a vertical plane. FIG. 4C illustrates edge and rod portions split into four. Obviously, the edge and rod portions can be split into three, or any other number, of suitable enlargements.

FIG. 5 shows a side view of a modification of the free end 16 of an inner arm 4. According to this embodiment, the enlargement of the edge portion 18 is made with the aid of a die, forming a semi-circular opening 28 at the end of the slot 22. The rod portion 20' remains without an enlargement. A circular opening may just as well be formed, corresponding to the configurations of FIG. 2 or 3, wherein both rod portions 20, 20' are made with enlargements.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An orthodontic facebow of the type having an inner bow consisting of two inner arms, each having an end portion, and an interconnected outer bow consisting of outer arms, characterized in that the free ends of each inner arm are split into a plurality of arm portions and at least one arm portion is fitted with a ratchet type enlargement so as to allow it to be easily inserted into a tube connected to a band affixed to a tooth, while preventing disengagement therefrom without at least one of said arm portions being squeezed towards the other or others.

2. The orthodontic facebow as claimed in claim 1, wherein the ends of each of said inner arms are split into two arm portions.

3. The orthodontic facebow as claimed in claim 1, wherein the ends of each of said inner arms are split into four arm portions.

4. The orthodontic facebow as claimed in claim 1, wherein the ends of each portion of each of said inner arms is bent, forming a knee, said knee acting as a detent delimiting the movement of the arm when it is inserted within the tube.

5. The orthodontic facebow as claimed in claim 2, wherein at least one of the end portions of said split arms is made with an enlargement by a die forming at least a semi-circular opening between the end portions of the split arms.

* * * * *